United States Patent
Wieland

(10) Patent No.: US 10,365,265 B2
(45) Date of Patent: Jul. 30, 2019

(54) METHOD FOR TESTING A BIOLOGICAL SAMPLE IN DOPING AND/OR DRUG TESTS

(71) Applicant: Eberhard Wieland, Stuttgart (DE)

(72) Inventor: Eberhard Wieland, Stuttgart (DE)

(*) Notice: Subject to any disclaimer, the term of this patent is extended or adjusted under 35 U.S.C. 154(b) by 647 days.

(21) Appl. No.: 14/695,721

(22) Filed: Apr. 24, 2015

(65) Prior Publication Data

US 2016/0238587 A1   Aug. 18, 2016

(30) Foreign Application Priority Data

Feb. 12, 2015   (DE) .................. 10 2015 001 872

(51) Int. Cl.
G01N 33/50 (2006.01)
G01N 33/487 (2006.01)
G01N 33/493 (2006.01)
A61B 10/00 (2006.01)

(52) U.S. Cl.
CPC ..... *G01N 33/48714* (2013.01); *G01N 33/493* (2013.01); *G01N 33/50* (2013.01); *A61B 10/007* (2013.01); *A61B 10/0038* (2013.01)

(58) Field of Classification Search
CPC . G01N 33/48714; G01N 33/493; G01N 33/50
See application file for complete search history.

(56) References Cited

U.S. PATENT DOCUMENTS

2005/0164998 A1   7/2005   Lomans et al.

OTHER PUBLICATIONS

Mareck et al. (J. Mass Spec., 2008, 43:877-891) (Year: 2008).*
Thevis et al. (Anal. Bioanal. Chem., 2007, 388:1539-1543) (Year: 2007).*
Castella et al. (FSI Genetics, 2007, pp. 281-282) (Year: 2007).*
Saugy, M., Lundby, C., Robinson, N., "Monitoring of Biological Markers Indicative of Doping: The Athlete Biological Passport," Br Journal Sports Med, Published Online First, Mar. 21, 2014, bjsm.bmj.com.
Van Renterghem, P., Polet, M., Brooker, L., Van Gansbeke, W., Van Eenoo, P., "Development of a GC/C/IRMS Method—Confirmation of a Novel Steroid Profiling Approach in Doping Control," Steroids, 77, 2012, 1050-1060, www.elsevier.com/locate/steroids.
Van Renterghem, P., Van Eenoo, P., Sottas, P.E., Saugy, M., Delbeke, F., "Subject-Based Steroid Profiling and the Determination of Novel Biomarkers for DHT and DHEA Misuse in Sports," Dec. 1, 2010, www.drugtestinganalysis.com.
Canadian Intellectual Property Office, "Examination Search Report," dated Aug. 23, 2016.

* cited by examiner

*Primary Examiner* — Jeremy C Flinders
(74) *Attorney, Agent, or Firm* — Emerson Thomson Bennett, LLC; Daniel A. Thomson

(57) ABSTRACT

The present teachings describe a method for testing a biological sample, including (a) obtaining a biological sample from a mammal, (b) acquiring at least two extracellular endogenous metabolic products from the biological sample, (c) detecting the at least two extracellular endogenous metabolic products from the extract, (d) determining a pattern on the basis of the presence or the mass ratio of the at least two extracellular endogenous metabolic products, (e) comparing the pattern with the pattern from a retention sample.

8 Claims, 6 Drawing Sheets

METHOD FOR TESTING A BIOLOGICAL SAMPLE IN DOPING AND/OR DRUG TESTS

FIELD

The present teachings relate to a method for testing a biological sample to trace body materials and/or excretions back to an individual.

BACKGROUND

To establish whether active pharmaceutical ingredients or narcotic drugs are present in an individual in the body, analyses in various body materials can be carried out in the laboratory. A laboratory analysis is generally required when abuse is suspected. This plays a role in addiction medicine, as in the case of drug abuse or medicament abuse or the checking of drug withdrawal, in the case of the monitoring of the absence of drugs in the workplace or in the case of forensic questions. When body materials (e.g. blood, urine, saliva, secretions, puncture fluids, tissue biopsies) are sent to an analytical laboratory, it is not always guaranteed that the sample sent can be unambiguously traced back to the individual from whom it actually originates. It is possible that accidental or intentional sample swapping or tampering occurs. This risk occurs especially in the case of urine samples, which are particularly suited to drug analysis, since they are acquired non-invasively and the medicaments and drugs and metabolites thereof excreted in urine are present in a higher concentration than in blood and can be detected for a long period. Also, the profile of the metabolites makes it possible to provide additional information relating to the metabolism in the body.

Whereas the investigator must be directly involved at the side of the test subject during the withdrawal of blood, saliva, puncture fluids and biopsies and a visual check thus takes place at least during the withdrawal of sample, this does not always occur during the collection of urine or the deposition of feces. Although questions relating to medicament abuse and drug abuse require that the urine body material typically used for analysis be surrendered in plain sight, this cannot always be ensured. The structural conditions need to be present and the privacy of the test subjects needs to be respected. However, in the absence of supervision, there is, specifically in the case of urine, an especially large risk of manipulation and, in particular, surrendering of a urine sample from another individual, i.e. a fraudulent sample.

To uncover material substitution, procedures have been established in which the individuals are required to orally ingest marker substances which are excreted via urine as parent substances or as metabolites in urine. If the marker substances or the metabolic products thereof are not detectable in the tested urine, it is suspected that a sample from another individual has been surrendered.

European patent No. 1 410 014 B1 describes a method which makes it possible for a sample taken from an excretion, from a mammal body fluid or as a tissue sample to be identified with regard to the origin of the sample.

German patent application DE 10 2008 061 174 describes a method for identifying biological samples.

SUMMARY

Viewed from a first perspective, the present teachings can provide a method in which a biological sample can be assigned to an individual without a waiting time, in which the biological sample can be taken non-invasively.

BRIEF DESCRIPTION OF THE DRAWINGS

Example arrangements are described hereinafter with reference to the accompanying drawings.

DETAILED DESCRIPTION

Figure 1:
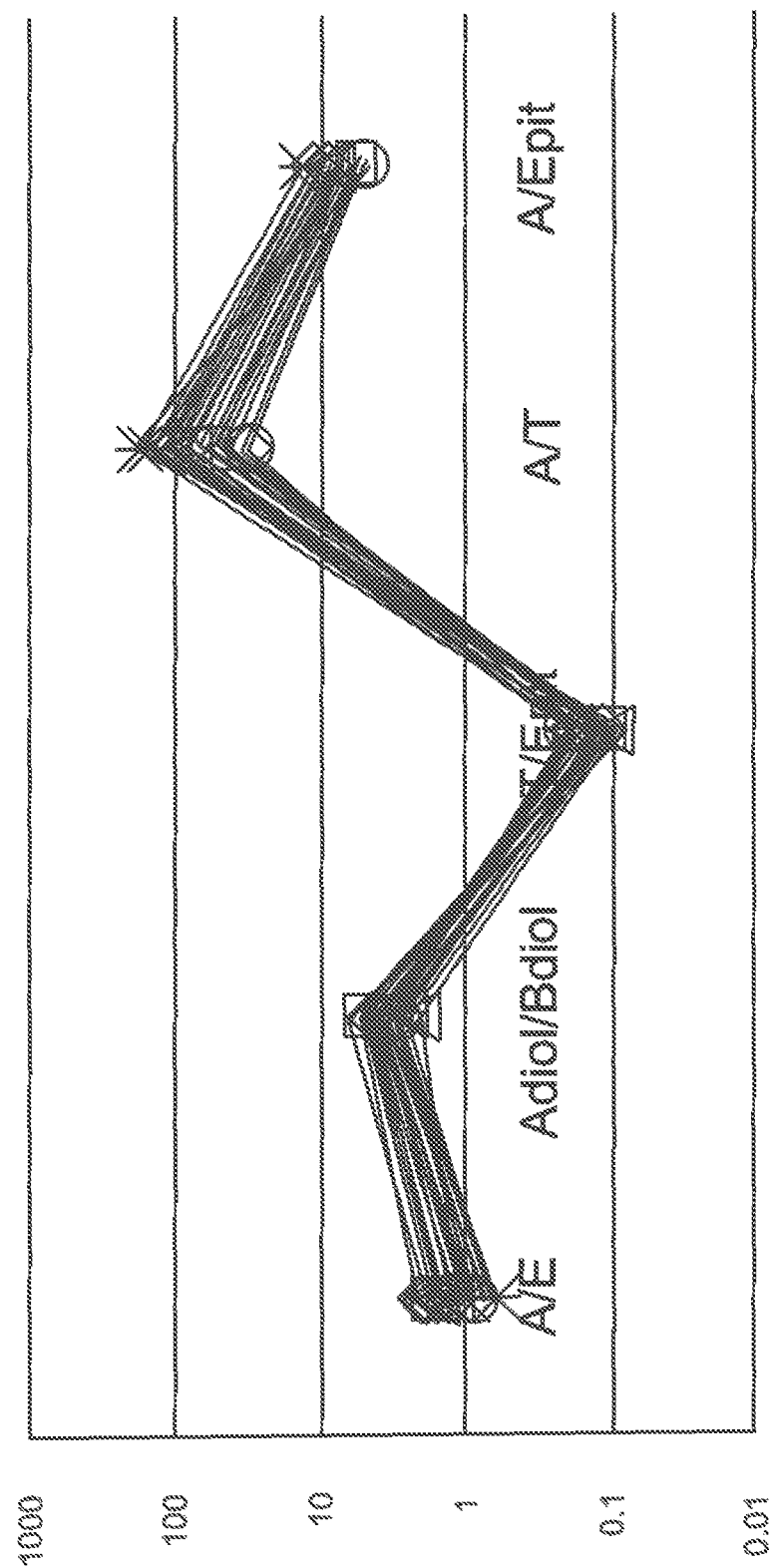
FIG. 1 shows a steroid profile of individual 1.

The present teachings provide a method for testing a biological sample, which method can be used for being able to trace the biological sample back to an individual. The method includes:

(a) obtaining a biological sample from a mammal,
(b) acquiring at least two extracellular endogenous metabolic products from the biological sample,
(c) detecting the at least two extracellular endogenous metabolic products from the extract,
(d) determining a pattern on the basis of the presence or the mass ratio of the at least two extracellular endogenous metabolic products,
(e) comparing the pattern with the pattern from a retention sample.

The biological sample used can be body materials or excretions, such as blood, urine, secretions, for example saliva, or other body fluids, and also tissue biopsies and hair. In one example, the biological sample is a urine sample, a saliva sample, a stool sample, or a mucosal swab. For questions in connection with the consumption of illegal drugs or medicaments or in the case of doping tests, urine is typically used.

The mammal in one example is a human. In this case, he or she can be a patient in a doctor's surgery or a hospital, a drug addict, a prisoner, a sportsperson, a workplace employee (workplace testing), or a person reapplying for a driving license.

The method is further suited to assigning biological samples in the case of animals, for example, in the case of pets or animals from agricultural use or livestock farming or sporting animals. Therefore, the biological sample can be animal body material in connection with, for example, veterinary questions from livestock farming or animal body material or excretions in connection with animals in high-performance sport, such as, for example, racehorses, racing camels, or greyhounds.

The biological sample can originate from humans and animals of either sex. A classic body material from a human is, for example, a urine sample from a drug addict involved in a substitution therapy with, for example, methadone, buprenorphine, L-polamidon, or diamorphine. In the case of individuals involved in a substitution program, it is normal to detect, on a regular basis, that said individuals are not consuming any other (illegal) drugs, and that the substitution substance is being ingested. This is done by an analysis of the urine for drugs and/or the metabolites thereof, and also of the substitution substance and/or its metabolites in appropriate intervals.

Laboratory tests for drug, alcohol, or medicament abnormalities are a part of the assessment of individuals who have lost their driving license as a consequence of driving a motor vehicle under the influence of drugs. Before the driving license is reissued, it is generally required to detect, on a regular basis, that said individuals have not consumed any drugs or medicaments over a relatively long period (e.g. several months). This is mainly done by the testing of urine or hair samples. In the penal system and in high-performance sports too, urine samples are frequently tested in humans and animals concerning the possible ingestion or administration of illegal substances.

The biological sample can be obtained in various ways (for example, step (a) of the method according to the present teachings). In one example, the biological sample is obtained non-invasively, and so sample collection does not require medical personnel to be present or to carry out. The biological sample can be excretions which are collected, such as, for example, urine. The biological sample can further be material acquired by means of a puncture procedure or a biopsy, such as, for example, blood or tissue samples. The biological material can further be obtained by means of a buccal swab or a hair sample. In one example, the biological sample is urine.

The extracellular endogenous metabolic product encompasses all products which, in a living or dead individual, are or have been self-produced biochemically as part of metabolism, in contrast to exogenously introduced substances. Chemically, they can be lipids, peptides, proteins, carbohydrates, extracellular nucleic acids, and steroids. In the context of the present teachings, steroids also encompass all derivatives of steroids or derivatives of sterane, such as cyclopentanoperhydrophenanthrene and also the isomers thereof.

In one example, the endogenous metabolic products are selected from androsterone, etiocholanolone, 5a-androstane-3a,17b-diol, 5b-androstane-3a,17b-diol, testosterone, and epitestosterone. In one example, the ratio, for example the mass ratio or the concentration of two or more of the metabolic products in the sample, is determined. The above listed metabolic products are not influenced by sporting activity, endurance sport, menstrual cycle, or circadian and annual rhythm. A distortion or manipulation of the sample can therefore be avoided or prevented.

In one example, the mass ratio of two metabolic products selected from androsterone/etiocholanolone, 5a-androstane-3a,17b-diol/5b-androstane-3a,17b-diol, testosterone/epitestosterone, androsterone/testosterone, and androsterone/epitestosterone is determined.

In one example, the mass ratio of at least two, at least three, at least four, or five mass ratios is determined, selected from androsterone/etiocholanolone, 5a-androstane-3a,17b-diol/5b-androstane-3a,17b-diol, testosterone/epitestosterone, androsterone/testosterone, and androsterone/epitestosterone.

Acquiring the extracellular endogenous metabolic product (for example, step (b) of the method according to the present teachings) is achieved by extraction, though other methods known in the prior art can also be used. Detection, i.e. for example the determination of the presence and/or the determination of the concentration and/or the determination of the ratio of the extracellular endogenous metabolic products, is typically done chromatographically (step (c) of the method according to the present teachings). Chromatographic methods encompass, inter alia, gas chromatography (GC), high-performance liquid chromatography (HPLC), mass spectrometry (MS), electrophoresis, and thin-layer chromatography (TLC), it also being possible to use combinations of two or more of said methods. Further methods for detecting the extracellular endogenous metabolic products encompass immunological methods such as, for example, the enzyme-linked immunosorbent technique, enzymatic methods such as, for example, a visual enzymatic assay or NMR spectroscopy.

In one example, the pattern of the presently described steroids, and/or steroid derivatives, such as the derivatives of cyclopentanoperhydrophenanthrene (sterane) and also the isomers thereof, is determined by a coupled gas chromatography-mass spectrometry method (GC-MS), HPLC-mass spectrometry method (HPLC-MS), HPLC method, or by gas chromatography (GC).

From the detected extracellular endogenous metabolic product(s), it is possible to create a pattern which allows the assignment of the biological sample from which the detection was performed to a particular individual (for example, step (d) of the method according to the present teachings). "Pattern" is to be understood to mean in particular the typical sequence of extracellular endogenous metabolic products such as the above-described steroids, steroid derivatives, or derivatives of cyclopentanoperhydrophenanthrene (sterane), the ratio thereof, and the mass ratio thereof, to one another, as described by Thevis, M. et al. (Anal Bioanal Chem 2007; 388: 1539-891) by way of example. In particular, a "pattern" can also be achieved by determining one or more metabolic products or ratios of metabolic products over a relatively long period, for example over several days, weeks, months, or years.

The pattern of the extracellular endogenous metabolic products is tested in the retention sample in the same body material, for example urine, in which the analysis in the biological sample is also carried out.

In a body material, the pattern of metabolic products, for example, the presently described steroids, is specific to an individual and thus allows the unambiguous assignment of a body material to an individual as a result of comparison of the patterns obtained (for example, step (e) of the method according to the present teachings). This is the case when urine is obtained as a biological sample. To this end, the presence and/or the concentration of the above-described at least two extracellular endogenous metabolic products in the biological sample is/are determined. The pattern can also result from the detection, i.e. the determination of, inter alia, the presence and/or concentration and/or the ratio, such as the mass ratio, of more than two, i.e. three, four or more, metabolic products.

If the comparison of the pattern of the extracellular endogenous metabolic products in the biological sample acquired under supervision (retention sample) results in an agreement with the pattern in the biological sample, it can be assumed that the biological sample can be unambiguously traced back to the individual. However, if there are discrepancies in the comparison, it must be assumed that the material was intentionally or unintentionally swapped or tampered with. In the case of urine samples, this can mean that, for example, someone else's urine was surrendered or substances having a tampering effect were added to the sample.

Therefore, using the method according to the present teachings, the acquisition of the biological sample, i.e. the surrendering of urine, only has to be carried out under supervision once in order to unambiguously establish the individual pattern of extracellular endogenous metabolic products. It is then no longer necessary for each further acquisition of a body material to be carried out under supervision. A waiting time of several hours, is not applicable. Likewise not applicable is the determination of a DNA sequence. This leads to considerable speeding-up of, and greater acceptance of, the entire method. Furthermore, the legal regulations and expensive and complicated molecular biology analysis are not applicable. To detect or rule out the consumption of illegal drugs or medicaments, it is helpful that biological samples such as body materials be reliably assigned to an individual in order to ensure the veracity of analytical results and to rule out both false-negative and false-positive results.

The method according to the present teachings provides the following:
1) possibility of non-invasive sample collection
2) low workload
3) convenient to perform
4) specific instruments not readily available in a toxicology laboratory are not required
5) no legal issues in terms of data protection
6) respecting the privacy of the test subject
7) can be carried out in the absence of medical personnel/advice
8) leads to unambiguous results even after relatively long sample storage The present teachings are described by means of the following examples.

EXAMPLES

Example 1: Traceability of a Urine Sample Containing Drug Residues to an Individual Example 1 concerns the collection of a urine sample, the shipping of the urine sample, the extraction of the urine sample, the detection of drug residues and the ascertainment of a steroid profile by means of gas chromatography-mass spectrometry (GC-MS).

Urine from an individual is collected in a commercially available plastic or glass vessel.

The sample vessel is clearly marked with a machine-readable barcode containing an order number which can also be found on the electronically readable sample dispatch note or has been generated by computer from an electronic order entry system. The name of the individual and the requested analysis are encoded in the order. The sample is sent to the laboratory, where the order is activated electronically. The request for the detection of a medicament or an illegal drug also automatically triggers the ascertainment of a so-called steroid profile (steroids, steroid derivatives, other derivatives of cyclopentanoperhydrophenanthrene).

In the laboratory, a portion of the urine sample for the GC-MS analysis is admixed with internal standards, hydrolysed at acidic pH and extracted with an organic solvent. To this end, the sample is adjusted to pH 5 with 0.1 M acetic acid and admixed with glucuronidase. Thereafter, internal standards (e.g. deuterated standards for mass spectrometry analysis), carbonate buffer and n-pentane are added. The sample is mixed and heated to 60° C. for 90 min. After cooling and centrifugation, 4 ml of the upper organic phase are vaporized. 100 µl of derivatization reagent (e.g. trimethylsilyl (TMS)) are added to the dried extract and mixed on a vortex mixer, and the tube is closed with a lid and placed in a heating block for 30 min at 60° C. After the extract has cooled down, it is provided for analysis, for example by injection into a GC-MS system. The pattern of steroids, steroid derivatives or other derivatives of cyclopentanoperhydrophenanthrene (sterane) and also the isomers thereof is evaluated in the computer of the analytical system.

In a second portion of the urine sample, the detection of a medicament, an illegal drug, or the metabolites thereof is conducted using generally recognized methods, which also include gas chromatography-mass spectrometry.

Figure 2:
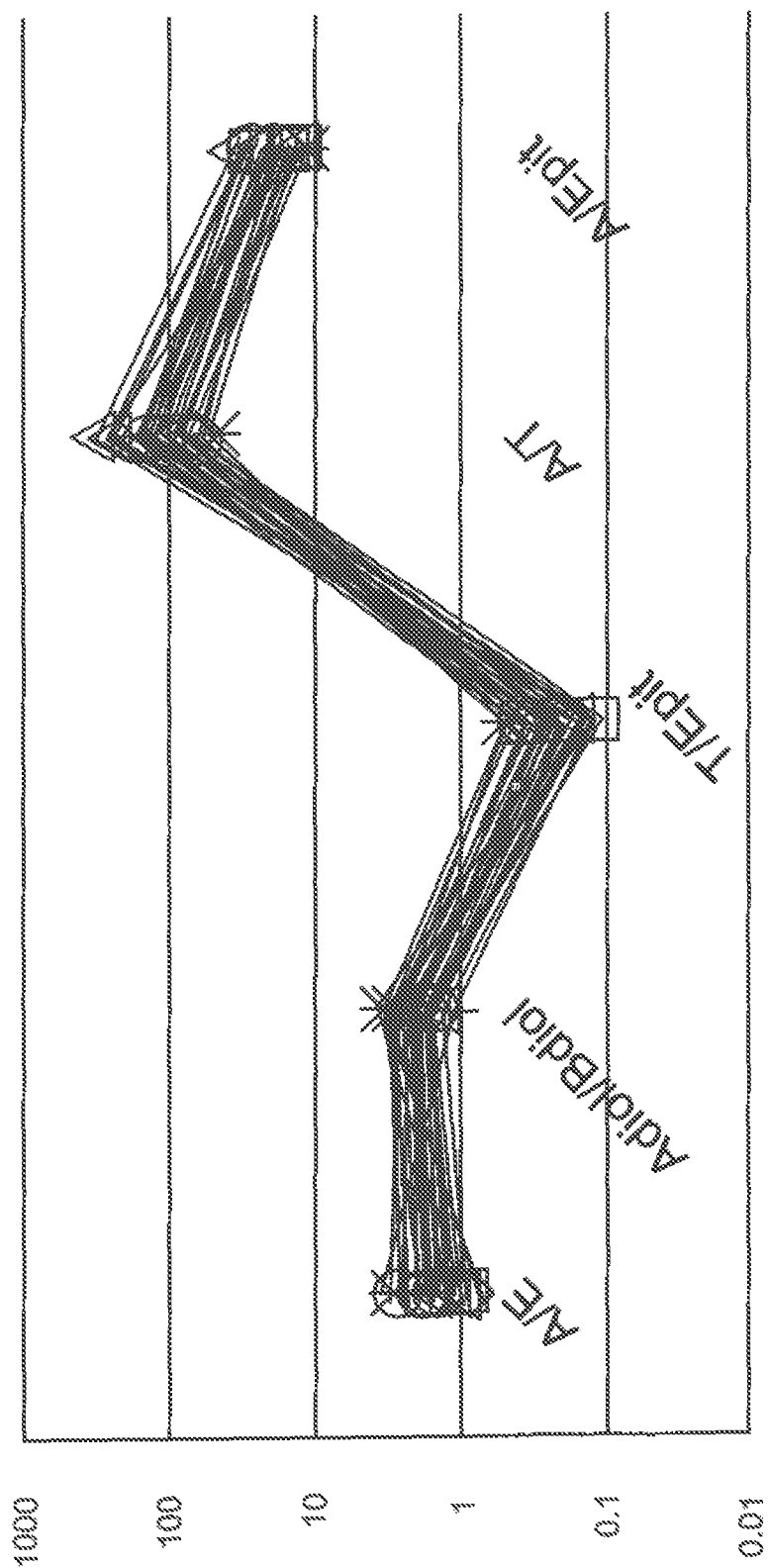
FIG. 2 shows a steroid profile of individual 2.
Figure 3:
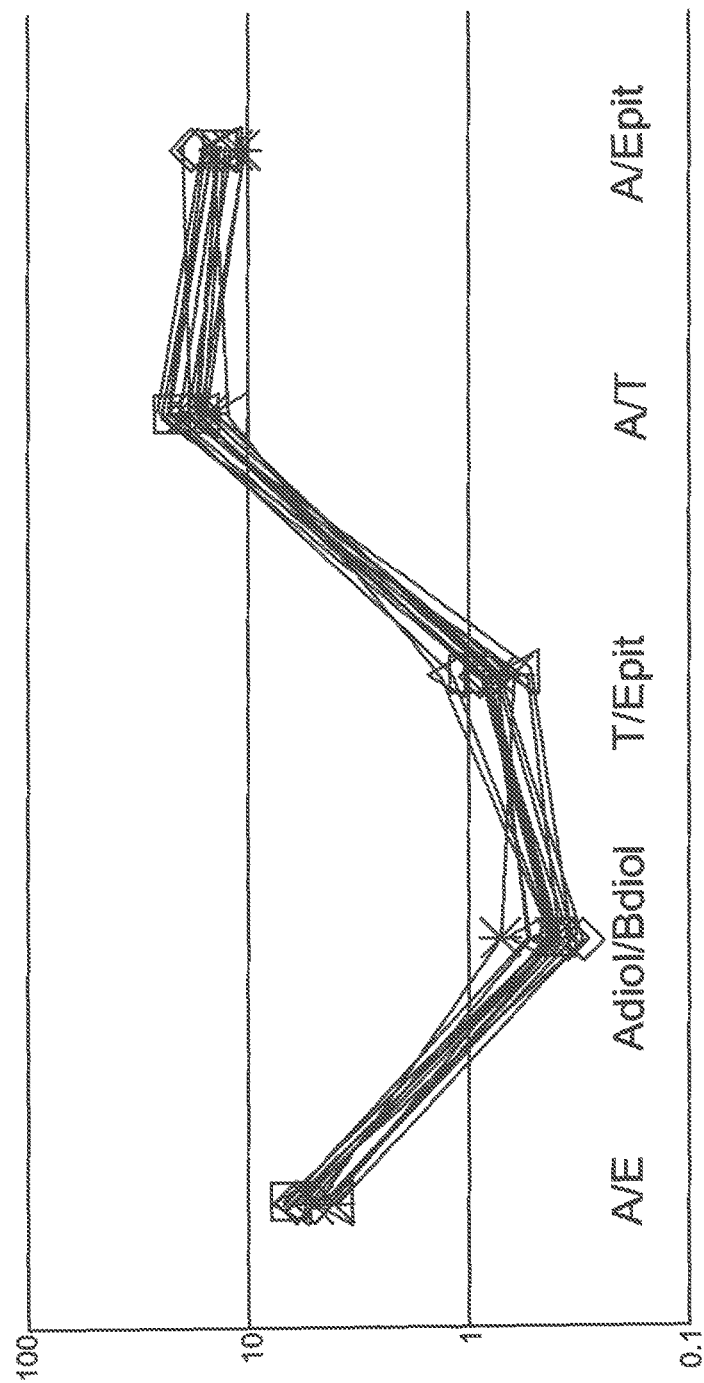
FIG. 3 shows a steroid profile of individual 3.
Figure 4:
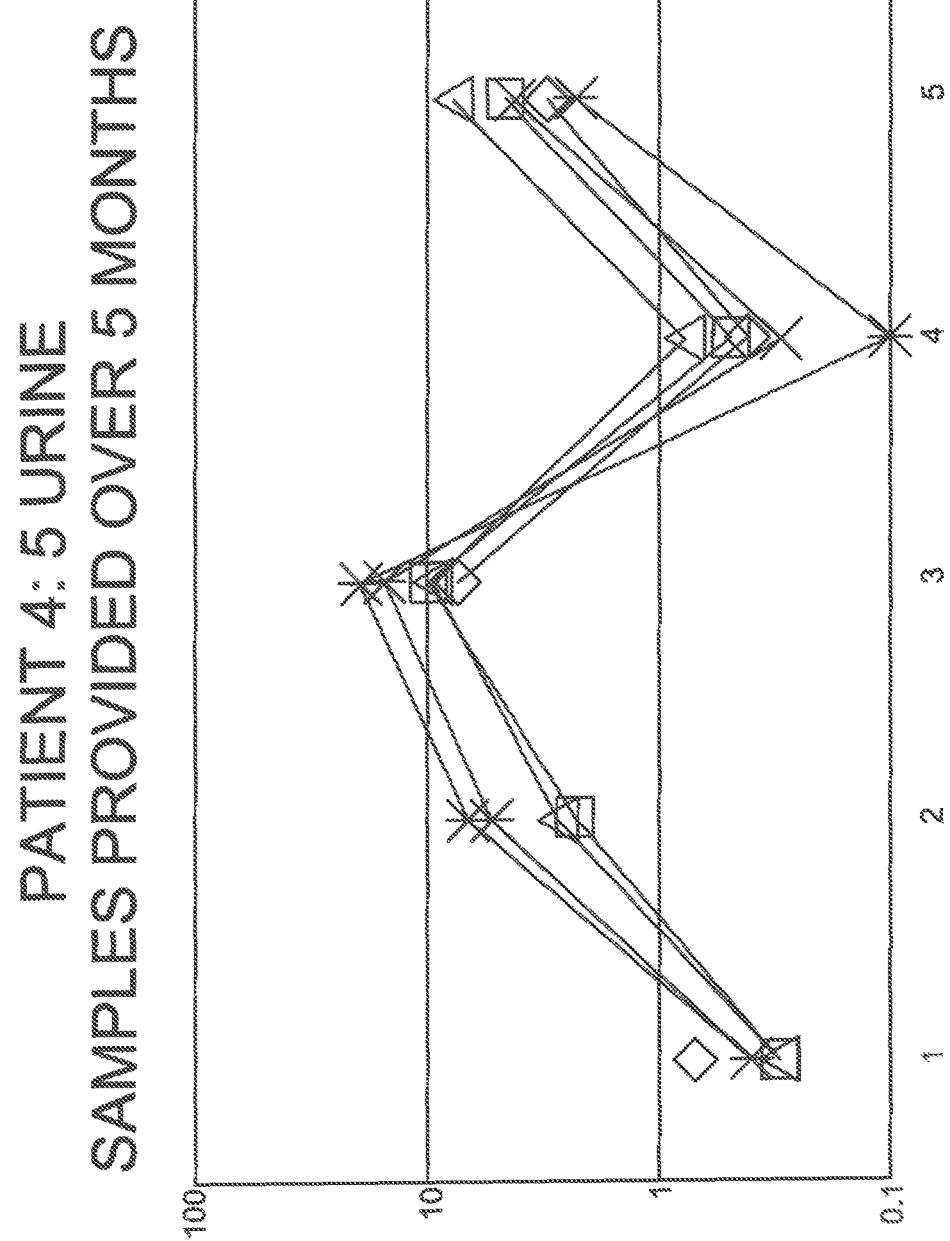
FIG. 4 shows a steroid profile of individual 4.
Figure 5:
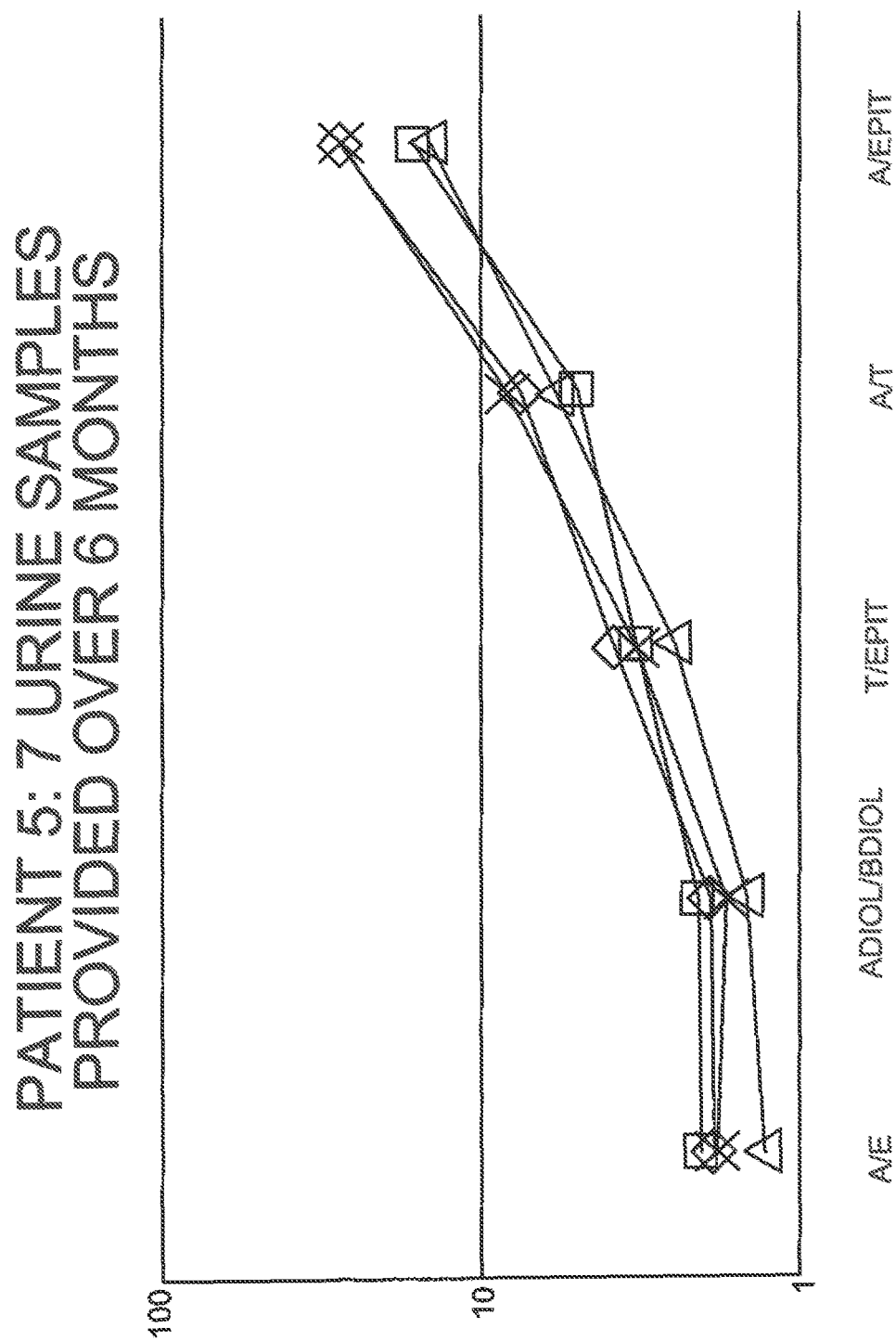
FIG. 5 shows the steroid profile of individual 5; and,
FIG. 6 shows the steroid profile of individual 6.
Figure 6:
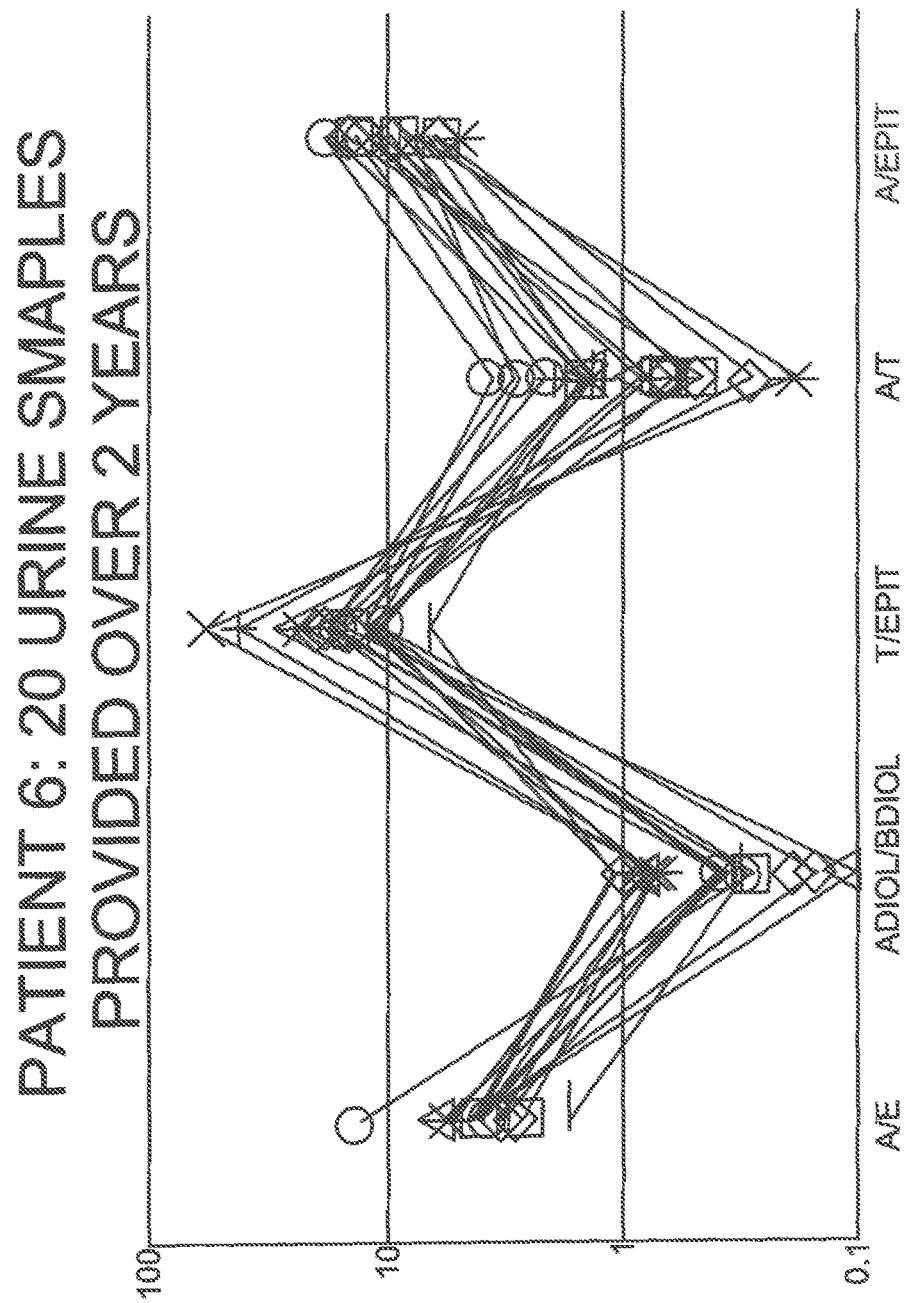

In the case of the first sample from an individual, the pattern of steroids, steroid derivatives or other derivatives of cyclopentanoperhydrophenanthrene (sterane) and also the isomers thereof is stored in the computer. In the case of a follow-up sample, the pattern is compared to the one which already exists. A typical pattern of steroids in test subjects (steroid profile) is shown in FIGS. 1-6.

Example 2: Identifying Urine Samples on the Basis of Endogenous Metabolic Products (Biomarkers)

The metabolic products are determined as described in Example 1.

The steroid hormones were analysed by means of mass spectrometry and the ratios of the steroids androsterone/etiocholanolone, 5a-androstane-3a,17b-diol/5b-androstane-3a,17b-diol, testosterone/epitestosterone, androsterone/testosterone, and androsterone/epitestosterone were plotted on a graph. Initially, the urine steroid profiles of 10 known individuals were created. Urine was collected again from the same individuals. The samples were anonymized and the urine steroid profiles determined, with the goal of assigning the anonymized samples to the 10 known individuals. Furthermore, the methodology was checked with respect to the checking of sample identity in the context of substitution therapy. In addition, the results were compared with the parallel creation of DNA profiles (NGM Select Kit, Applied Biosystems).

The 10 anonymized samples from the initial experiment could be unambiguously assigned to the corresponding individuals. 49 urine samples assigned on the basis of steroid profiles were compared using DNA profiles (patient consent obtained in accordance with the GenDG (genetic diagnostics act)). From these samples, 13 samples were not evaluable because the DNA concentration was too low, 35 samples showed concordant assignment, and one sample was incorrectly assigned on the basis of the steroid profile.

Further on, the use of the urine steroid profiles was applied to 100 substitution patients over a period of two years. The steroid profiles determined at various times for some example patients are shown in FIGS. 1 to 6. It was found that the use of the steroid profile tested is very highly suited to assigning a surrendered urine sample to a retention sample from a particular individual.

The use of the urinary steroid profiles in substitution therapy therefore allows, as shown in the examples, the individual assignment of urine samples. Assignment using DNA profiles is more meaningful from a forensic point of view because of the relatively high interindividual variability, but exhibits a very much greater failure frequency, since it is highly dependent on the DNA concentration. By contrast, the use of the urinary steroid profile gives the addiction physician an additional measure of reliability in substitution therapy.

The present teachings have been described, hereinabove. It will be apparent to those skilled in the art that the above methods and apparatuses may incorporate changes and modifications without departing from the general scope of present teachings. It is intended to include all such modifications and alterations insofar as they come within the scope of the appended claims or the equivalents thereof. Although the description above contains much specificity, this should not be construed as limiting the scope of the present teachings, but as merely providing illustrations of some of the examples of the present teachings. Various other examples and ramifications are possible within its scope.

The foregoing detailed description is given primarily for clearness of understanding and no unnecessary limitations are to be understood therefrom, for modification will become obvious to those skilled in the art upon reading this disclosure and may be made upon departing from the spirit of the present teachings and scope of the appended claims. Accordingly, the present teachings are not intended to be limited by the specific exemplifications presented hereinabove. Rather, what is intended to be covered is within the spirit and scope of the appended claims.

Furthermore, notwithstanding that the numerical ranges and parameters setting forth the broad scope of the present teachings are approximations, the numerical values set forth in the specific examples are reported as precisely as possible. Any numerical value, however, inherently contain certain errors necessarily resulting from the standard deviation found in their respective testing measurements.

What is claimed is:

1. A method for assignment of a urine sample to a particular individual, comprising the steps of:
   (a) obtaining a urine sample from a human involved in a drug substitution program, a drug withdrawal program, or work place testing, wherein the urine sample is obtained non-invasively;
   (b) acquiring extracellular endogenous metabolic products from the urine sample;
   (c) detecting the extracellular endogenous metabolic products from the extract, wherein the metabolic products are detected by gas chromatography, high-performance liquid chromatography, mass spectrometry, electrophoresis, thin-layer chromatography, immunological methods, enzymatic methods, NMR spectroscopy, or a combination of two or more thereof;
   (d) determining a first pattern on the basis of the presence or the mass ratio of the extracellular endogenous metabolic products;
   (e) comparing the first pattern with a second pattern from a retention sample;
   (f) assigning the urine sample to the particular individual on the basis of a result of the comparison of the first pattern with the second pattern from the retention sample obtained in step e), wherein only the retention sample is acquired under supervision; and
   (g) performing a drug test on the urine sample.

2. The method of claim 1 wherein no determination of a DNA sequence of the human is done.

3. The method of claim 2, wherein the urine sample is assigned to the particular individual with at least 97% accuracy, wherein the endogenous metabolic products are selected from androsterone, etiocholanolone, 5a-androstane-3a,17b-diol, 5b-androstane-3a,17b-diol, testosterone, and epitestosterone, wherein the mass ratio of the metabolic products is determined, selected from androsterone/etiocholanolone, 5a-androstane-3a,17b-diol/5b-androstane-3a, 17b-diol, testosterone/epitestosterone, androsterone/testosterone, and androsterone/epitestosterone.

4. A method for assignment of a biological sample to a particular individual, comprising the steps of:
   (a) obtaining a urine sample from a human involved in a drug, substitution program, a drug withdrawal program, or work place testing, wherein the urine sample is obtained non-invasively;
   (b) acquiring extracellular endogenous metabolic products from the urine sample, wherein the endogenous metabolic products are selected from androsterone, etiocholanolone, 5a-androstane-3a,17b-diol, 5b-androstane-3a,17b-diol, testosterone, and epitestosterone;
   (c) detecting the extracellular endogenous metabolic products from the extract;
   (d) determining a first pattern on the basis of the presence or the mass ratio of the extracellular endogenous metabolic products, wherein the mass ratio of the metabolic products is determined, selected from androsterone/etiocholanolone, 5a-androstane-3a,17b-diol/5b-androstane-3a,17b-diol, testosterone/epitestosterone, androsterone/testosterone, and androsterone/epitestosterone;
   (e) comparing the first pattern with a second pattern from a retention sample; and
   (f) assigning the urine sample to the particular individual, wherein the assignment of the urine sample to the particular individual is done on the basis of a result of the comparison of the first pattern with the second pattern from the retention sample obtained in step e); and
   (g) performing a drug test on the urine sample.

5. The method of claim 4, wherein the metabolic products are detected by gas chromatography, high-performance liquid chromatography, mass spectrometry, electrophoresis, thin-layer chromatography, immunological methods, enzymatic methods, NMR spectroscopy, or a combination of two or more thereof.

6. The method of claim 5, wherein only the retention sample is acquired under supervision.

7. The method of claim 6, wherein the urine sample is assigned to the particular individual with at least 97% accuracy.

8. The method of claim 7, wherein no determination of a DNA sequence of the human is done.

* * * * *